US00PP16611P3

(12) United States Plant Patent
Devor

(10) Patent No.: US PP16,611 P3
(45) Date of Patent: Jun. 6, 2006

(54) CLIMBING SHRUB ROSE PLANT NAMED 'RADSUNSAR'

(50) Latin Name: *Rosa hybrida*
Varietal Denomination: Radsunsar

(75) Inventor: William Devor, Arroyo Grande, CA (US)

(73) Assignee: CP Delaware, Inc., Wilmington, DE (US)

( * ) Notice: Subject to any disclaimer, the term of this patent is extended or adjusted under 35 U.S.C. 154(b) by 121 days.

(21) Appl. No.: 10/957,635

(22) Filed: Oct. 5, 2004

(65) Prior Publication Data

US 2006/0075527 P1 Apr. 6, 2006

(51) Int. Cl.
*A01H 5/00* (2006.01)

(52) U.S. Cl. ..... Plt./111
(58) Field of Classification Search ..... Plt./111
See application file for complete search history.

*Primary Examiner*—Anne Marie Grunberg
*Assistant Examiner*—Annette H Para
(74) *Attorney, Agent, or Firm*—Buchanan Ingersoll PC

(57) ABSTRACT

A new and distinct variety of climbing rose plant is provided which forms in abundance on a substantially continuous basis attractive clusters of semi-double informal clear yellow blossoms having approximately ten petals on average. The new variety is a spontaneous mutation of unknown causation of the 'Radsun' variety (U.S. Plant Pat. No. 13,063). The climbing growth habit can be readily distinguished from the free-standing growth habit of the 'Radsun' variety. Vigorous vegetation is formed. The foliage is dense medium green with a satin finish. Excellent resistance to Black Spot is displayed. Attractive dense ornamentation in the form of foliage and blossoms is made possible when the new variety is grown on a support.

2 Drawing Sheets

Figures 1, 2, 3, 4, 5, 6, 7, 8, 9, 10, 11, 12, 13, 14, 15, 16, 17:
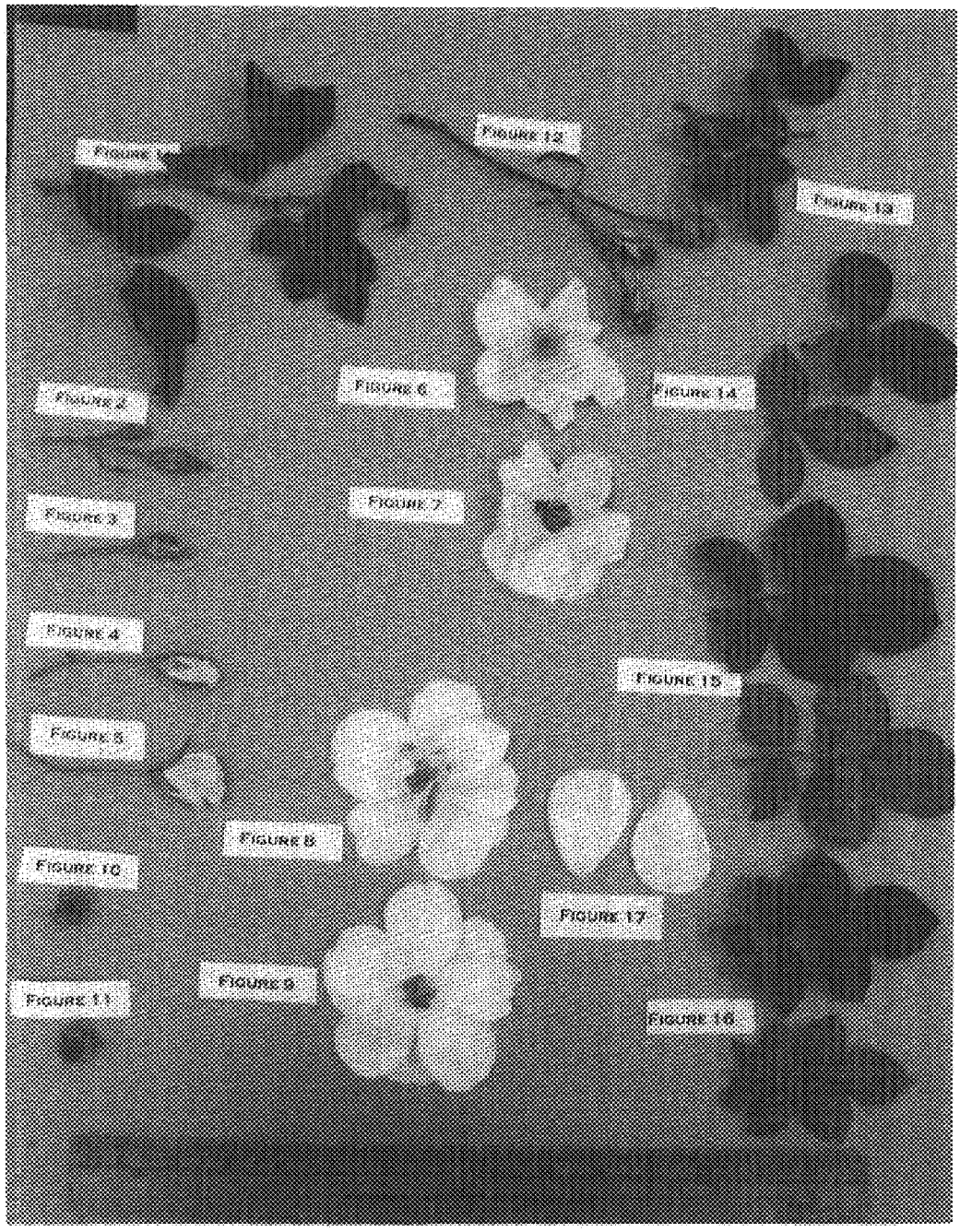

Botanical/commercial classification: *Rosa hybrida*/ Climbing Shrub Rose Plant.
Varietal denomination: cv. 'Radsunsar'.

SUMMARY OF THE INVENTION

The new variety of *Rosa hybrida* climbing shrub rose plant of the present invention was discovered during August, 2002 while present among a block of rose plants of the 'Radsun' variety (U.S. Plant Pat. No. 13,063) growing in a greenhouse setting at Arroyo Grande, Calif., U.S.A. I was attracted to the new variety primarily because of its distinctive growth habit that was unlike that of the parental variety. The new variety is believed to be a spontaneous naturally-occurring mutation of the 'Radsun' variety of unknown causation. Had I not discovered and preserved the original plant of the new variety it would have been lost to mankind.

It was found that the new variety of climbing shrub rose plant of the present invention possesses the following combination of characteristics:

(a) abundantly forms on a substantially continuous basis attractive clusters of semi-double informal blossoms that are clear yellow in coloration, (b) exhibits an upright climbing growth habit, (c) forms vigorous vegetation, (d) forms dense medium green foliage having a satin finish, and (e) exhibits excellent resistance to Black Spot.

The new variety well meets the needs of the horticultural industry. It can be grown to advantage as attractive ornamentation in parks, gardens, public areas, and residential landscapes. It is particularly well suited for growing in the landscape when informal ornamentation is desired. The clear yellow blossoms contrast nicely with the medium green foliage having a satin finish.

The new variety of *Rosa hybrida* of the present invention can be readily distinguished from its 'Radsun' parent. More specifically, the growth habit of the 'Radsun' variety is free-standing and commonly assumes a height of one meter or more. On the contrary the growth habit of the new variety of the present invention is climbing and requires a support. Also, the blossoms of the 'Radsun' variety tend to display a slightly darker and brighter Lemon Yellow coloration.

The new variety also can be readily distinguished from the 'Golden Showers' (U.S. Plant Pat. No. 1,557) and 'Meivalier' (U.S. Plant patent application Ser. No. 10/776,247, filed Feb. 12, 2004) climbing rose varieties. 'Golden Showers', unlike the new variety, forms double yellow flowers having a sweet and honey-like fragrance and extremely long canes. 'Meivalier', unlike the new variety, forms double apricot-orange blossoms having a slight citrus fragrance and has not demonstrated the formation of hips.

The characteristics of the new variety have been found to be homogeneous and stable and to be strictly transmissible at West Grove, Pa., U.S.A. by asexual propagation, such as budding, grafting, and the rooting of cuttings. The characteristics of the new variety are transmitted true to type from one generation to another by such asexual propogation. The plant propagates well and grows very well on its own roots.

The new variety has been named the 'Radsunsar' variety. The new variety is being marketed under the CLIMBING CAREFREE SUNSHINE trademark.

BRIEF DESCRIPTION OF THE PHOTOGRAPHS

The accompanying photographs show, as nearly true as it is reasonably possible to make the same in color illustrations of this character, typical specimens of the plant parts of the new variety, as well as a specimen of a typical plant of the new variety while growing in the landscape. The rose plants of the new variety illustrated herein were four years of age and were grown in a greenhouse at West Grove, Pa., U.S.A. while grafted on *Rosa* 'Dr. Huey' rootstock (non-patented in the United States). The photographs were prepared on Apr. 9, 2002. Dimensions in inches are indicated at the bottom of FIGS. 1 to 17.

Figure 18:
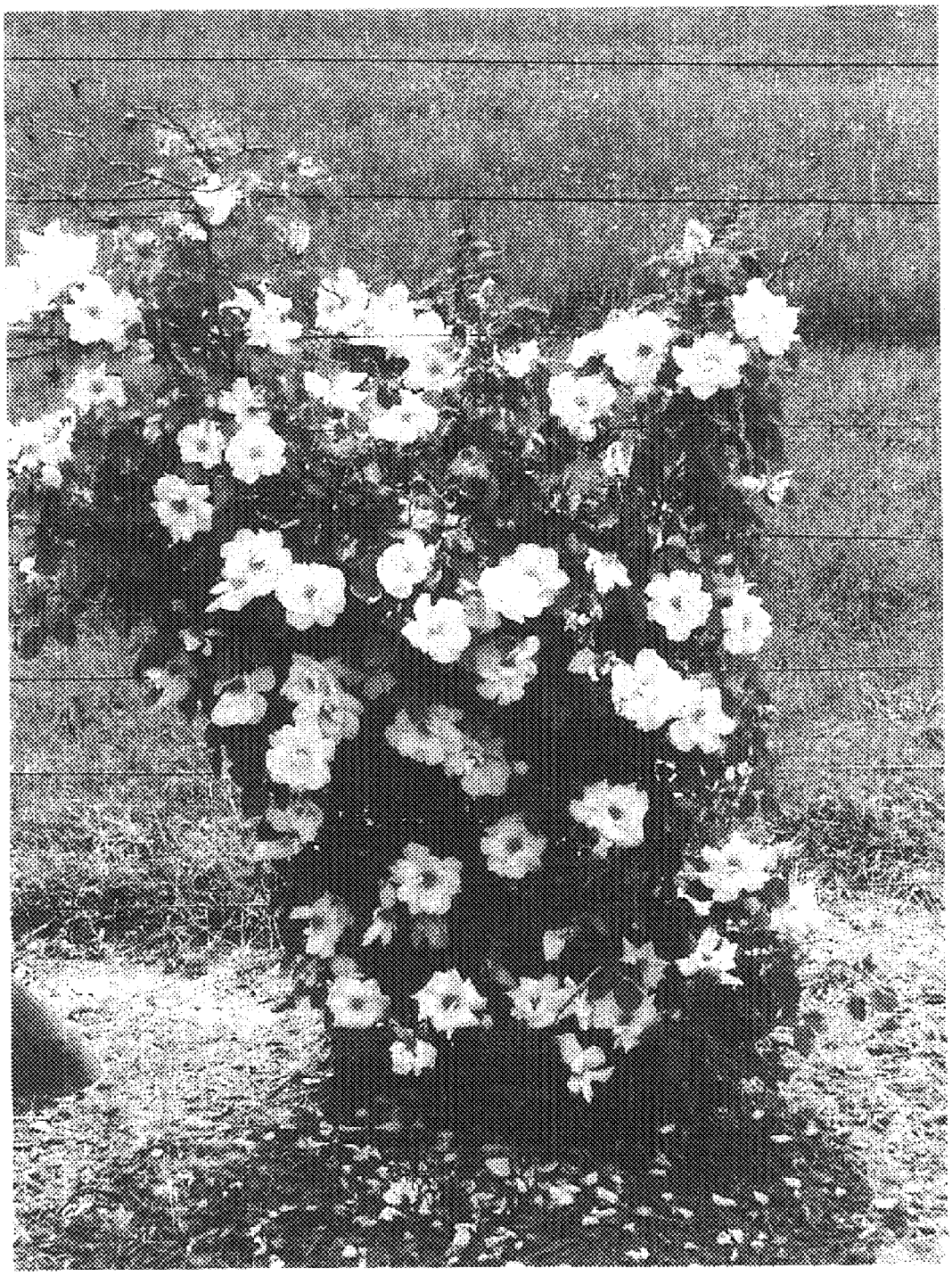

FIG. 1—illustrates a specimen of a young shoot with leaves;

FIG. 2—illustrates a specimen of a floral buds before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plain view—obverse;

FIG. 7—illustrates a specimen of an open flower—plain view—reverse;

FIG. 8—illustrates a specimen of a fully open flower—plain view—obverse;

FIG. 9—illustrates a specimen of a fully open flower—plain view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem following petal drop;

FIG. 13—illustrates a specimen of a main branch with foliage;

FIG. 14—illustrates specimens of leaves with three leaflets—plan view—upper surface (top), and under surface (bottom);

FIG. 15—illustrates specimens of leaves with five leaflets—plan view—upper surface (top), and—plan view—under surface (bottom);

FIG. 16—illustrates specimens of leaves with seven leaflets—plan view—upper surface (top), and—plan view—under surface (bottom);

FIG. 17—illustrates specimens of two maturing petals with upper surface being shown at the left, and the under surface being shown at the right; and FIG. 18—illustrates specimens of a typical flowering plant while being grown in the landscape with the support of a wire fence.

DETAILED DESCRIPTION

The chart used in the identification of colors is that of The Royal Horticultural Society (R.H.S. Colour Chart), London, England. The description is based on the observation of two year-old specimens of the new variety during October while growing outdoors on their own roots near West Grove, Pa., U.S.A.

Class: Climbing Shrub Rose.

Plant:

*Height.*—Approximately 6 to 7 feet on average at the end of the growing season when grown on a support.

*Width.*—Approximately 4 to 5 feet on average at the end of the growing season when grown on a support.

*Habit.*—Upright and climbing shrub.

Branches:

*Color.*—Young stems: Yellow-Green Group 144B with some flecks of Greyed-Purple Group 184B. Adult wood: Yellow-Green Group 144B.

*Thorns.*—Size: approximately 5 to 8 cm in length on average. Shape: needle-shaped. Quantity: commonly approximately 25 true thorns on average per 30 cm of stem. Color: Greyed-Yellow Group 161C with highlights of Red Group 51B.

Leaves:

*Stipules.*—Parallel with the auricle facing outward.

*Petioles.*—Upper surface: Yellow-Green Group 144B. Under surface: Yellow-Green Group 144B with flecks of Greyed-Purple Group 184C.

*Rachis.*—Glandular and commonly with small prickles on the upper surface. The prickle size commonly varies from approximately 1 to 3 mm with up to 4 prickles on the rachis of three-leaflet leaves and up to 7 prickles on the rachis of seven-leaflet leaves. The prickles commonly are slightly recurved and tend to point towards the stem. The glands commonly are globose and reddish in coloration and are present on both surfaces while borne on short stalks of approximately 0.3 mm in length.

*Leaflets.*—Number: 3, 5, and 7. Shape: ovate with a rounded base, and an acuminate tip. Margins: regular serration. Texture: smooth and consistent. Overall appearance: very dense, and medium green in coloration with a satiny finish. Color (young foliage): upper surface: Yellow-Green Group 146A with a tint of Greyed-Purple Group 184D at the edges. Under surface: Yellow-Green Group 146B with a tint of Greyed-Purple Group 184D at the edges. Color (adult foliage): Upper surface: Green Group 139A. Under surface: Yellow-Green Group 146C. Midrib: commonly bears glands on the ventral surface that are similar to those present on the rachis as well as small prickles that are approximately 0.4 to 0.8 mm in length.

Inflorescence:

*Number of flowers.*—Commonly approximately 4 blooms per floral stem on average in a cluster.

*Peduncle.*—Yellow-Green Group 144B with some prickles, and approximately 5 cm in length on average.

*Sepals.*—Upper surface: commonly between Yellow-Green Group 144A and Yellow-Green Group 144B. Under surface: commonly between Yellow-Green Group 144B and 144C with pubescence of White Group 155D.

*Buds.*—Shape: ovoid. Length: approximately 2.5 cm on average. Size: small to medium. Color (when opening): Upper surface: Sulphur Yellow, near Yellow Group 6A and 6C shading to near Yellow Group 7B and Yellow Group 9A towards the base. Under surface: near Yellow Group 7B and Yellow Group 8A shading to near Yellow Group 6A and Yellow Group 7A towards the base.

*Flower.*—Form: semi-double and informal. Diameter: approximately 8 cm. on average. Color (when opening begins): Upper surface: Sulphur Yellow, near Yellow Group 6A and 6C shading to near Yellow Group 7B and Yellow Group 9A towards the base. Under surface: near Yellow Group 7B and Yellow Group 8A shading to Yellow Group 6A and Yellow Group 7A towards the base. Color (when blooming): Upper surface: Dresden Yellow, near Yellow Group 5C shading to near Yellow Group 5B towards the base. Under surface: Sulphur Yellow, near Yellow Group 6D shading to near Yellow Group 7D towards the base. Color (at end of blooming): upper surface: near Green-Yellow Group 1D and Yellow Group 2D shading to Yellow Group 7D towards the base. Under surface: near Yellow Group 2D shading to Yellow Group 4C towards the base. Fragrance: slightly spicy. Petal form: wedge-shaped with a curled apex. Petal number: approximately 10 on average. Petaloids: sometimes observed at a frequency of approximately 1 to 5 per bloom, at more commonly at a frequency of 1 to 3 per bloom. Petal drop: very good, the petals drop cleanly and freely. Stamen number: approximately 70 on average. Anthers: Greyed-Orange Group 163C in coloration. Filaments: Yellow Group 12B in coloration. Pistils: number approximately 30 on average. Stigmas: Yellow-Orange Group 20A in coloration. Styles: Yellow Group 12B with highlights of Red Group 52A in coloration. Receptacle: separate and free with achenes on the bottom and wall.

Development:

*Vegetation.*—Commonly vigorous and strong with the level of vigor being influenced by the environmental conditions that are encountered.

*Blossoming.*—Abundant and substantially continuous.

*Resistance to diseases.*—Excellent with respect to Black Spot.

*Formation of hips/seeds.*—Hips are formed. Hips length 20–25 mm. Hips width 18–22 mm. Hips color During September Yellow 145A with some area near Orange Group 22A. Late Fall and Winter the entire hip is Orange Group 22A.

Plants of the 'Radsunsar' variety have not been observed under all possible environmental conditions to date. Accordingly, it is possible that the phenotype may vary somewhat with variations in the environment, such as temperature, light, etc.

I claim:

1. A new and distinct variety of climbing shrub rose plant characterized by the following combination of characteristics:

(a) abundantly forms on a substantially continuous basis attractive clusters of semi-double informal blossoms that are clear yellow in coloration, (b) exhibits an upright climbing growth habit, (c) forms vigorous vegetation, (d) forms dense medium green foliage having a satin finish, and (e) exhibits excellent resistance to Black Spot;

substantially as herein shown and described.

* * * * *